US012723979B2

(12) United States Patent
Hanke

(10) Patent No.: US 12,723,979 B2
(45) Date of Patent: Sep. 1, 2026

(54) SYSTEM AND A METHOD FOR CLASSIFYING A SAMPLE INTO ONE OF AT LEAST TWO TYPES OF POLYAMIDE

(71) Applicant: TRINAMIX GMBH, Ludwigshafen am Rhein (DE)

(72) Inventor: Michael Hanke, Ludwigshafen am Rhein (DE)

(73) Assignee: TRINAMIX GMBH, Ludwigshafen am Rhein (DE)

( * ) Notice: Subject to any disclaimer, the term of this patent is extended or adjusted under 35 U.S.C. 154(b) by 69 days.

(21) Appl. No.: 18/690,499

(22) PCT Filed: Oct. 11, 2022

(86) PCT No.: PCT/EP2022/078186
§ 371 (c)(1),
(2) Date: Mar. 8, 2024

(87) PCT Pub. No.: WO2023/061977
PCT Pub. Date: Apr. 20, 2023

(65) Prior Publication Data

US 2024/0369478 A1 Nov. 7, 2024

(30) Foreign Application Priority Data

Oct. 12, 2021 (EP) .................................... 21202116

(51) Int. Cl.
*G01N 21/35* (2014.01)
*G01N 21/359* (2014.01)
(Continued)

(52) U.S. Cl.
CPC ........... *G01N 21/359* (2013.01); *G01N 33/36* (2013.01); *G01N 33/442* (2013.01); *G01N 2201/1293* (2013.01); *Y02W 30/62* (2015.05)

(58) Field of Classification Search
CPC .... G01N 21/359; G01N 33/36; G01N 33/442; G01N 2201/1293; Y02W 30/62
See application file for complete search history.

(56) References Cited

U.S. PATENT DOCUMENTS 5,807,490 A * 9/1998 Davis .................... B29C 48/304 210/322
2014/0186477 A1* 7/2014 Dell'Orco ............... B02C 23/38 241/43

FOREIGN PATENT DOCUMENTS

CN 112693032 A 4/2021
CN 113049528 A 6/2021
(Continued)

OTHER PUBLICATIONS

Page from https://www.thermofisher.com/order/catalog/product/MICROPHAZIRPC#/MICROPHAZIRPC, accessed and printed on Jul. 19, 2024.

(Continued)

*Primary Examiner* — Mark R Gaworecki
(74) *Attorney, Agent, or Firm* — Armstrong Teasdale LLP

(57) ABSTRACT

Disclosed herein is a method for classifying a sample into one of at least two types of polyamide. The method includes the following steps:

a) providing at least one sample, where the sample includes at least one type of polyamide;
b) acquiring at least one spectrum of the sample using at least one near-infrared spectrometer device;
c) determining at least one peak from the at least one spectrum; and
d) classifying the sample depending on the at least one peak determined from the at least one spectrum into one of the at least two types of polyamide.

14 Claims, 3 Drawing Sheets

(51) Int. Cl.
*G01N 33/36* (2006.01)
*G01N 33/44* (2006.01)

(56) References Cited

FOREIGN PATENT DOCUMENTS

| | | | | |
|---|---|---|---|---|
| JP | H06308022 A | | 11/1994 | |
| JP | 2005249624 A | | 9/2005 | |
| JP | 2019086412 A | | 6/2019 | |
| WO | WO-0165243 A1 | * | 9/2001 | ........... G01N 33/367 |

OTHER PUBLICATIONS

International Search Report for PCT/EP2022/078186, mailed Dec. 7, 2022, 4 pages.
Written Opinion for PCT/EP2022/078186, mailed Dec. 7, 2022, 5 pages.
Geller et al., "Using MEMS Technology for Cost Effective Recycling of Plastics", Proc. of SPIE, vol. 6466, pp. 1-7 (2007).

* cited by examiner

SYSTEM AND A METHOD FOR CLASSIFYING A SAMPLE INTO ONE OF AT LEAST TWO TYPES OF POLYAMIDE

CROSS-REFERENCE TO RELATED APPLICATIONS

This application is a U.S. National Phase Application of International Patent Application No. PCT/EP22/78186, filed Oct. 11, 2022, which claims priority to European Patent Application No 21202116.6 filed Oct. 12, 2021, and each of which is hereby incorporated by reference herein.

FIELD OF THE INVENTION

The invention relates to a method and a system for classifying a sample into one of at least two types of polyamide as well as a use of a near-infrared spectrometer device for classifying a sample into one of at least two types of polyamide. The method and system specifically may be applied for a non-destructive and on-site analysis of polyamide samples. However, further fields of application of the present invention may be feasible.

PRIOR ART

Polyamide (PA) samples, specifically samples of the subclasses PA 6 and PA 6.6, may reveal a very similar visual and mechanical appearance. Hence, plastic recyclers and manufacturers in their process monitoring commonly desire means for distinguishing the two plastic types.

Currently, the polyamides to be classified can for example be analyzed through a melting point test employing different melting points of the materials. The melting test may come with the drawback that destructive and time-consuming testing is implied. An alternative would be a performance of a chemometric analysis using a mid-infrared (MIR) spectrometer. This prohibits rapid on-site testing without any time delay and requires expensive laboratory equipment.

Thus, there is a need for an on-site and non-destructive analysis technique. Near-infrared (NIR) spectroscopy can principally offer a viable pathway to achieve this. Yet, NIR spectra, specifically in the range from 1400 nm to 2500 nm, of Polyamide samples, specifically of Polyamide samples which are attributable to the subclass of either PA 6 or PA 6.6, commonly exhibit a strong variation with respect to parameters which differ from a latter subclass. These parameters may specifically be or may include a sample color, a surface texture, a surface structure. Other parameters may also be feasible.

The device "microPHAZIR PC" from Thermo Scientific is suitable for handheld carpet fiber identification. More information on the device may be found on https://www.thermofisher.com/order/catalog/product/MICROPHAZIRPC#/MICROPHAZIRPC.

In Geller Y: "Using mems technology for cost effective recycling of plastics", Proc. of SPIE, Vol. 6466, 2007, pages 646604-1-646604-07, XP040235480, a development and demonstration of a Micro-Electro-Mechanical-System (MEMS) based handheld material analyzer to efficiently identify plastic materials for the recycling industry is described.

In JP 2005 249624 A, a polymer group classification method by optical spectrum capable of precisely classifying unknown polymeric materials into respective material types is described.

In CN 113 049 528 A, a near infrared spectrum-based fiber component identification method and module is described. The near infrared spectrum-based fiber component identification method comprises the steps of a) establishing an identification model, b) pre-processing before classification and c) performing a classification and identification algorithm. The near infrared spectrum-based fiber component identification module comprises a fiber component identification system software.

In CN 112 693 032 A, a high-throughput intelligent sorting method for recovering waste plastic is described. The method comprises the following steps that (1) a high-throughput intelligent sorting system is arranged, and screening manipulators are sequentially arranged from top to bottom in a layered manner from a hopper to form a multi-layer infrared screening production line; (2) the recovered mixed waste plastic fragments are conveyed to all infrared screening manipulators for spectrum recognition sorting and sorting; (3) step (2) is repeated, the recovered mixed waste plastic fragments are sequentially fed into all the infrared screening manipulators to complete a first sorting cycle; (4) subsequent sorting circulation is carried out on the remaining unrecognized mixed waste plastic until all the waste plastic is sorted; and (5) the single-component waste plastic is enabled to be separately used for subsequent regeneration processing.

Problem Addressed by the Invention

Therefore, a problem addressed by the present invention is that of providing a method and a system for classifying a sample into one of at least two types of polyamide as well as a use of a near-infrared spectrometer device for classifying a sample into one of at least two types of polyamide which at least substantially avoid the disadvantages of known methods and systems of this type.

In particular, it is desirable to provide a method and a system for classifying a sample into one of at least two types of polyamide which enable an on-site and non-destructive analysis of polyamide as well as a reliable classification into at least two types of polyamide.

SUMMARY OF THE INVENTION

This problem is solved by the present invention with the features of the independent patent claims. Advantageous developments of the invention, which can be implemented individually or in combination, are presented in the dependent claims and/or in the following specification and detailed embodiments.

As used herein, the expressions "have", "comprise" and "contain" as well as grammatical variations thereof are used in a non-exclusive way. Thus, the expression "A has B" as well as the expression "A comprises B" or "A contains B" may both refer to the fact that, besides B, A contains one or more further components and/or constituents, and to the case in which, besides B, no other components, constituents or elements are present in A.

In a first aspect of the present invention, a method for classifying a sample into one of at least two types of polyamide is disclosed. The method according to the present invention comprises the following steps, which may, preferably, be performed in the given order or in a different order. Further, additional steps might be provided which are not listed. Unless explicitly indicated otherwise, any or all of the steps can be performed simultaneously, at least partially.

Further, any or all of the steps can be performed at least twice, especially in a repeatedly fashion.

The method according to the present invention comprises the following steps:

a) providing at least one sample, wherein the sample comprises at least one type of polyamide;
b) acquiring at least one spectrum of the sample using at least one near-infrared spectrometer device;
c) determining at least one peak from the at least one spectrum; and
d) classifying the sample depending on the at least one peak determined from the at least one spectrum into one of the at least two types of polyamide.

The method may specifically be a computer-implemented method. The term “computer implemented method” as used herein may refer, without limitation, to a method involving at least one computer and/or at least one computer network. The computer and/or computer network may comprise at least one processor which may be configured for performing at least one of the method steps, specifically at least one of steps b), c) and d), of the method according to the present invention. The method may be performed completely automatically, specifically without user interaction. The term “automatically” as used herein may refer, without limitation, to a process which is performed completely by means of at least one computer and/or computer network and/or machine, in particular without manual action and/or interaction with a user.

As used herein, the term “providing” refers to an arbitrary step of a method wherein a desired object is made available. Thus, in step a) of the method according to the present invention the sample may be made available. Thus, step a) may correspond to a provision step. As further used herein, the term “sample” refers to an arbitrary object which, fully or partially, comprises polyamide. Specifically, the object may have at least one surface, fully or partially, comprising at least one type of polyamide. The sample may have an arbitrary shape. Further, the sample may be an hand-held-able object. However, the sample may also be or may be part of an unmovable component such as of a building component. Thus, the near-infrared spectrometer device which will further be described below in more detail may specifically be a handheld near-infrared spectrometer device which may be brought to the unmovable component.

As further used herein, the term “polyamide” refers to an arbitrary polymer with repeating units linked by amide bonds. Polyamides may occur both naturally and artificially. Artificially made polyamides may be manufactured through step-growth polymerization or solid-phase synthesis yielding materials such as nylons, aramids, and sodium poly (aspartate). Synthetic polyamides are commonly used in textiles, automotive industry, carpets, kitchen utensils and sportswear due to their high durability and strength. According to the composition of their main chain, synthetic polyamides may be classified into aliphatic polyamides, polyphthalamides, and aromatic polyamides.

The aliphatic polyamides may include polyamide 6 and polyamide 6.6. Polyamide 6 may also be referred to as nylon 6 or polycaprolactam. Polyamide 6 may refer to a semicrystalline polyamide which is formed by ring-opening polymerization of ε-caprolactam. When ε-caprolactam is heated at about 533 K in an inert atmosphere of nitrogen for about 4 to 5 hours, the ring may break and may undergo polymerization. During polymerization, the amide bond within each ε-caprolactam molecule may be broken, with active groups on each side re-forming two new bonds as the monomer becomes part of the polymer backbone. Unlike polyamide 6.6 in which a direction of the amide bond reverses at each bond, the polyamide 6 amide bonds may lie in a same direction. Polyamide 6 may specifically be provided as fibers. Polyamide 6.6 may also be referred to as nylon 6.6, nylon 66, nylon 6-6, nylon 6/6 or nylon 6,6. Polyamide 6.6 may be made of two monomers each comprising six carbon atoms, hexamethylenediamine and adipic acid. Polyamide 6.6 may be synthesized by polycondensation of hexamethylenediamine and adipic acid. Equivalent amounts of hexamethylenediamine and adipic acid may be combined with water in a reactor. This may be crystallized to make nylon salt, an ammonium/carboxylate mixture. The nylon salt may go into a reaction vessel where polymerization process takes place either in batches or continuously. Removing water may drive the reaction toward polymerization through a formation of amide bonds from the acid and amine functions. Thus molten polyamide 6.6 may be formed. It may either be extruded and granulated or may directly be spun into fibers by extrusion through a spinneret and cooling to form filaments.

As outlined above, in step b), the at least one spectrum of the sample is acquired using the at least one near-infrared spectrometer device. As generally used, the term “spectrum” refers to a partition of the optical spectral range, in particular, the infrared (IR) spectral range, especially at least one of the near-infrared (NIR) or the mid-infrared (MidIR) spectral ranges. Each part of the spectrum may be constituted by an optical signal which may be defined by a signal wavelength or wavenumber and the corresponding signal intensity. As used herein, the term “acquiring” is understood by the skilled person as referring to settling on, concluding on, or ascertaining a fact and/or data. Thus, “acquiring a spectrum” may relate to measuring optical signals, specifically recording, and optionally storing on a suitable storage device, data points representing the optical signal of the near-infrared spectrometer device.

Specifically, step b) may comprise determining, and optionally storing on a storage medium, data points representing an absorbance signal, specifically over a wavenumber. The term “absorbance” may refer to a common logarithm of a ratio of incident to transmitted radiant power through a material. Specifically, the absorbance may refer to a spectral absorbance corresponding to a common logarithm of the ratio of incident to transmitted or reflected spectral radiant power through a material. The term “wavenumber” as used in spectroscopy may be defined as a number of wavelengths per unit distance, typically centimeters ($cm^{-1}$). Specifically, the spectrum may be acquired in a region of 6250 $cm^{-1}$ to 6550 $cm^{-1}$. Further, specifically, the spectrum may be acquired in a region of 6150 $cm^{-1}$ to 6550 $cm^{-1}$.

As used herein, the term “spectrometer device” may refer to an apparatus which is capable of recording the signal intensity with respect to the corresponding wavelength of a spectrum or a partition thereof, such as a wavelength interval, wherein the signal intensity may, preferably, be provided as an electrical signal which may be used for further evaluation. The spectrometer device may, specifically, comprise at least one optical element, especially selected from at least one of an optical filter or a dispersive element. Herein, the dispersive element may, preferably be selected from at least one of a prism, a grating, a length variable filter, or an interferometer. However, other embodiments may also be feasible. The optical element may be designed for receiving incident light and transferring the incident light to a detector array. Further, the optical element may be designated for separating the incident light into a spectrum of constituent wavelength signals.

Further, the spectrometer device may comprise at least one detector array. The detector array may, specifically, be separated from the optical element by a transparent gap and may comprise a plurality of detector elements. Each detector element may be designated for receiving at least a portion of one of the constituent wavelength signals. Further, the detector array may be configured to generate at least one detector signal depending on an illumination of the plurality of the detector elements by the at least one portion of one of the constituent wavelength signals. The detector elements, may, preferably, be arranged in a single line as a one-dimensional matrix along the length of the optical element, or, as an alternative, in more than one line, especially as two, three, or four parallel lines, in form of a two-dimensional matrix, in particular, in order to receive most of the intensity of the constituent wavelength signals as possible. Further, alternatively, the spectrometer device may comprise at least one single detector, specifically in case there are moving parts such as in an interferometer. However, also other embodiments may be feasible.

As further used herein, the term "light", generally, refers to a partition of electromagnetic radiation which is, usually, referred to as "optical spectral range" and which comprises one or more of the visible spectral range, the ultraviolet spectral range and the infrared spectral range. The term "visible", generally, refers to electromagnetic radiation having a wavelength of 380 nm to 760 nm. The terms "infrared" or "IR", generally, refer to electromagnetic radiation having a wavelength of 760 nm to 1000 μm, wherein a wavelength of 760 nm to 3 μm is, usually, denominated as "near infrared" or "NIR" while the wavelength of 3μ to 15 μm is, usually, denoted as "mid infrared" or "MidIR" and the wavelength of 15 μm to 1000 μm as "far infrared" or "FIR". Light used for the typical purposes of the present invention is, in particular, light in the IR spectral range, preferably in at least one of the NIR or the MidIR spectral ranges, more preferred having a wavelength of 1 μm to 5 μm, preferred of 1 μm to 3 μm, especially of 1.5 μm to 1.6 μm, approximately corresponding to a wavenumber of 6250 $cm^{-1}$ to 6550 $cm^{-1}$. The light which may, preferably, be emerging from an object can originate in the object itself, but can also optionally have a different origin, preferably at least one illumination source, and propagate from this origin to the object and subsequently towards the spectrometer device. The light which is propagating from the object to the spectrometer device may be light which may be reflected by the object and/or a reflective unit connected to the object. Thus, the spectrum may be acquired in a reflectance mode. Alternatively or in addition, the light may at least partially travel through the object.

Optionally, the method may comprise at least one preprocessing step. Specifically, the preprocessing step may comprise preprocessing the spectrum before step c) is conducted. Typically, NIR spectra comprise a mix of diffuse and specular reflectance or straight transmittance. A shape of a spectrum may be affected by different factors. Firstly, different wavelengths of the incident light may experience different absorption by the sample, specifically due to a chemical nature of the sample itself. Secondly, differences in a particle size of a material may cause light to be deviated at different angles depending on its wavelength. Scattering effects, along with possible differences in path length may constitute major causes of variations in NIR spectra. Thirdly, path length differences from sample to sample due to variations in positioning and/or irregularities in the sample surface may occur. Scattering effects may be both additive and multiplicative. Additive effects such as path length differences may produce a baseline displacement of the spectrum along a vertical axis, while multiplicative effects may modify a local slope of the spectrum. Thus, the term "preprocessing the spectrum" may refer to a correction of the spectrum with the purpose of eliminating or at least reducing effects which are unrelated to the chemical nature of the sample, but which may specifically depend on a sample morphology and a measurement geometry.

Specifically, the preprocessing step may comprise at least one technique selected from the group consisting of: a scatter correction technique; a derivative technique.

The scatter correction technique may be selected from the group consisting of: a multiplicative scatter correction (MSC); a standard normal variate transform (SNV); a robust normal variate transform (RNV); a range scaling; a pareto scaling. Also other scatter correction techniques may be feasible.

MSC may require a reference spectrum. The reference spectrum may refer to a spectrum which is ideally free from scattering effects. Exemplarily, an average spectrum $X_a$ may be taken as a reference spectrum. As particle size and path length effects may vary randomly from sample to sample, the average spectrum may reasonably reduce these effects. Specifically, the MSC may be conducted in two steps. Firstly, each spectrum X may be regressed against the average spectrum: $X_i \approx a_i + b_i X_a$. Secondly, a corrected spectrum may be calculated:

$$X_i^{msc} = (X_i - a_i)b_i.$$

SNV may be conducted on each individual spectrum. Thus, a reference spectrum may not be required. The SNV correction may be conducted in two steps. Firstly, each spectrum X may be mean centered by taking away its mean $\overline{X}_i$. Secondly, each mean centered spectrum may be divided by its own standard deviation:

$$X_i^{snv} = \left(X_i - \overline{X}_i\right) / \sigma_i.$$

RNV may work in a similar way as SNV: Instead of the means, a percentile, specifically a selectable percentile, may be applied. Instead of the usual standard deviation, a standard deviation of values which are below the percentile may be applied.

Further, the derivative technique may be selected from the group consisting of: a Norris derivative filter, specifically a first-order derivation, specifically a second-order derivation; a Savitzky-Golay derivation. Also other derivative techniques may be feasible.

The Norris derivative filter may also be referred to as Norris-Williams (NW) derivation. The Norris derivative filter may be configured for avoiding a noise inflation in finite differences. The Norris derivative filter may specifically include two steps. Firstly, a spectrum may be smoothed whereby averaging over a given number of points is performed:

$$x_{smooth,i} = \frac{\sum_{j=-m}^{m} x_{org,i+j}}{2\,m+1}.$$

Thereby, m may correspond to a number of points in a smoothing window centered around a current measurement point i. Secondly, for a first-order derivation, a difference between two smoothed values with a given gap size between them (larger than zero) may be taken:

$$x_i' = x_{smooth,i+gap} - x_{smooth,i-gap}.$$

For a second-order derivation, the smoothed value at point i and the smoothed value at a gap distance on either side may be taken twice:

$$x_i'' = x_{smooth,i-gap} - 2 \cdot x_{smooth,i} + x_{smooth,i+gap}.$$

Exemplarily, the second derivative of the Norris derivative filter may be applied with a window size of 15 pixels. The window size of 15 pixels may be applied in a very specific case of a spectral standardization which may be conducted for spectra from devices where a 8 $cm^{-1}$ pixel spacing may be enforced. Hence, any different choice of spacing may require entirely different window sizes.

Further, a baseline correction may be conducted before step c) is conducted. The baseline correction may be part of the preprocessing step or may be performed as an additional step. NIR spectra may often exhibit a baseline offset and a curvilinear trend caused, for example, by changes in an illumination angle or an optical path length. The baseline correction may be configured for resetting NIR spectra on a common baseline. Specifically, the baseline may be computed by a fitting, specifically by a linear fitting or by a polynomial fitting. However, also other methods may be feasible. Thereafter, a baseline corrected spectrum may be obtained by removing the baseline from the spectrum.

Exemplarily, an iterative restricted least squares algorithm may be applied. The algorithm may comprise a primary smoothing, repeated baseline suppressions and regressions with a second derivative constraint. Exemplarily, the following regularization parameters may be applied: second derivative constraint for main smoothing=6; second derivative constraint for secondary smoothing=4; weighting of positive residuals=0.1. However, also other regularization parameters may be feasible.

Specifically, the following steps may be conducted before step c) is performed:

i. performing the at least one baseline correction;
ii. performing the at least one scatter correction, specifically by performing the robust normal variate transform; and/or
iii. applying the at least one derivative technique, specifically applying the Norris derivative filter, more specifically applying the second derivative of the Norris derivative filter.

As outlined above, in step c), the at least one peak from the at least one spectrum is determined. As used herein, the term "peak" refers to at least one local maximum or its derivative of a spectrum. Furthermore, also minima in between the maxima, i.e., the maxima of a negative spectrum, may be fitted. As used herein, the term "determining a peak" refers to an arbitrary process including one or more of a peak detection, a peak finding, a peak identification, a peak fitting, a peak evaluation. Specifically, the term may refer to a qualitative determination of the peak such as a determination of a presence or an absence of the peak and/or to a quantitative determination of the peak such as determining a position of the peak. The peak determination may be an automatic peak determination, i.e. a peak determination performed by at least one computer and/or computer network and/or machine. Specifically, the automatic peak determination may be performed without manual action or interaction with a user. Specifically, in step c) a fitting procedure of at least a part of the spectrum may be performed. Specifically, the fitting procedure may be performed by using at least one mathematical operation and/or mathematical algorithm for determining the peak. Specifically, the fitting procedure may include an application of a second-order polynomial and, specifically, an employing of a zero-crossing point of its first derivative. Specifically, in step c), a peak in a region between 6300 $cm^{-1}$ and 6500 $cm^{-1}$, specifically in a region between 6350 $cm^{-1}$ and 6450 $cm^{-1}$, may be determined. Further, specifically, in step c), a peak in a region between 6150 $cm^{-1}$ and 6500 $cm^{-1}$ may be determined.

As outlined above, in step d), the sample is classified depending on the at least one peak determined from the spectrum into one of the at least two types of polyamide. As used herein, the term "classifying" refers to a process, typically denoted as "classification process", of sorting the at least one sample into at least two classes according to at least one parameter related to the at least one sample. Herein, the term "class", generally, refers to different types of the sample which may differ from each other by at least one material property and/or by a chemical structure of at least one material of the sample. Specifically, the type of polyamide may be selected from: polyamide 6; polyamide 6.6. However, also other types of polyamide may be feasible. Reference may be made to the description above.

Classifying the sample may comprise an assignment of at least one numerical value of a property of a peak to at least one pre-defined interval. Specifically, step d) may comprise classifying the sample depending on a position of the at least one peak determined from the spectrum. Specifically, the numerical value of the property of the peak may correspond to a wavenumber. Thereby, the pre-defined interval may correspond to a pre-defined interval of wavenumbers. Specifically, classifying the sample may comprise an assignment of the position of the at least one peak determined from the spectrum to the at least one pre-defined interval.

Specifically, classifying the sample may comprise an assignment of the at least one numerical value of the property of a peak to at least one first pre-defined interval or to at least one second pre-defined interval. Further, classifying the sample may comprise an assignment of the wavenumber to at least one third pre-defined wavenumber interval. The terms "first pre-defined interval", "second pre-defined interval" and "third pre-defined interval" may be considered as nomenclature only, without numbering or ranking the named intervals, without specifying an order and without excluding a possibility that several kinds of first pre-defined intervals, second pre-defined intervals and third pre-defined intervals may be present. Further, additional pre-defined intervals may be present. The term "pre-defined" may generally refer to a property of being determined, stated or fixed before a certain event occurs or is introduced. Specifically, one or more default values of the pre-defined intervals may be used and stored in a data storage device of an evaluation device. Further, the values of the pre-defined intervals may be manually adjustable by a user.

Specifically, the first pre-defined interval may include wavenumbers between 6380 $cm^{-1}$ and 6397 $cm^{-1}$, specifically between 6385 $cm^{-1}$ and 6395 $cm^{-1}$. Further, the second pre-defined interval may include wavenumbers between 6400 $cm^{-1}$ and 6430 $cm^{-1}$, specifically between 6405 $cm^{-1}$ and 6425 $cm^{-1}$. Further, the third pre-defined wavenumber interval may include wavenumbers between 6395 $cm^{-1}$ and 6405 $cm^{-1}$, specifically between 6397 $cm^{-1}$ and 6400 $cm^{-1}$. However, also other intervals may be feasible.

Depending on the preprocessing, the peaks may be in different places. For example, peaks of a second derivative may be systematically shifted from peaks of a first derivative or a non-derivative spectrum. In general, peaks within a wavenumber interval of 6200 $cm^{-1}$ and 6550 $cm^{-1}$ may be determinable. The actual intervals may depend very much on the selected preprocessing procedure. Further, the peak positions may depend on a spectral pixel width. Different NIR devices with different resolutions may deliver different values.

The assignment of the at least one numerical value of the property of a peak to the first pre-defined interval or to the second pre-defined interval may include classifying the sample into one of at least two types of polyamide. Specifically, the assignment of the at least one numerical value of the property of a peak to the first pre-defined interval may include classifying the sample into polyamide 6.6. Further, the assignment of the at least one numerical value of the property of a peak to the second pre-defined interval may include classifying the sample into polyamide 6. Further, the assignment of the at least one numerical value of the property of a peak to the third pre-defined interval may lead to an unsuccessful classification. Specifically, the at least one numerical value of the property of a peak may not be definitely assignable to one type of polyamide.

Optionally, the method may further comprise at least one confirmation step. The confirmation step may comprise classifying the sample depending on at least one further property of the spectrum, specifically of at least one further numerical value of the further property of the spectrum, which differs from the peak of the spectrum. Specifically, the confirmation step may comprise determining at least one first mean absorbance within at least one first pre-defined wavenumber interval. Further, the confirmation step may comprise determining at least one second mean absorbance within at least one second pre-defined wavenumber interval. Specifically, the first pre-defined wavenumber interval may include wavenumbers between 6294 $cm^{-1}$ and 6366 $cm^{-1}$. Further, the second pre-defined wavenumber interval may include wavenumbers between 6406 $cm^{-1}$ and 6494 $cm^{-1}$. However, also other wavenumber intervals may be feasible.

The terms "first pre-defined wavenumber interval" and "second pre-defined wavenumber interval" may be considered as nomenclature only, without numbering or ranking the named intervals, without specifying an order and without excluding a possibility that several kinds of first pre-defined wavenumber intervals and second pre-defined wavenumber intervals may be present. Further, additional pre-defined wavenumber intervals may be present. The first pre-defined wavenumber interval and the second pre-defined wavenumber interval may respectively be different or may be equivalent to the first pre-defined interval, the second pre-defined interval or the third pre-defined interval as outlined above. Further, the first pre-defined wavenumber interval and the second pre-defined wavenumber interval may respectively overlap with the first pre-defined interval, the second pre-defined interval or the third pre-defined interval as outlined above.

The confirmation step may comprise an assignment of the first mean absorbance to one of at least two first mean absorbance intervals. Further, the confirmation step may comprise an assignment of the second mean absorbance to one of at least two second mean absorbance intervals.

The assignment of the first mean absorbance to one of at least two first mean absorbance intervals and/or the assignment of the second mean absorbance to one of at least two second mean absorbance intervals may lead to a confirmation of classifying the sample into one of at least two types of polyamide.

In a further aspect of the present invention, a system for classifying a sample into one of at least two types of polyamide is disclosed. As further used herein, a "system for classifying a sample into one of at least two types of polyamide" refers to an apparatus which, in addition to the spectrometer device as outlined above, may comprise an evaluation device which is designated for determining spectral information, which may be related to a spectrum of the object, by evaluating detector signals provided by the detector array of the spectrometer device.

The system comprises at least one near-infrared spectrometer device. The near-infrared spectrometer device is configured for acquiring at least one spectrum of a sample. For further details on the near-infrared spectrometer device, reference to the description above is made. Further, the system comprises at least one evaluation device. The evaluation device is configured for determining at least one peak from the at least one spectrum and for classifying the sample depending on the at least one peak determined from the at least one spectrum into one of the at least two types of polyamide.

The term "evaluation device" may generally refer to an arbitrary component which is designed to actuate the near-infrared spectrometer device and/or to record signals from the near-infrared spectrometer device and/or to derive at least one item of information of the sample from the signals and/or to evaluate these signals in whole or part. The evaluation device may also be referred to as control part or as electronics unit. Thus, the evaluation device may specifically be or may comprise an electronic component. The electronic component may be configured for one or more of performing a measurement with the near-infrared spectrometer device, recording measurement signals, storing measurement signals or measurement data, transmitting signals or measurement data to another device. Thus, the electronic component specifically may comprise at least one of: a voltmeter, an amperemeter, a potentiostat, a voltage source, a current source, a signal receiver, a signal transmitter, an analog-digital converter, an electronic filter, an energy storage device, a data processing device, such as a microcontroller. Other embodiments of the electronic component are feasible. The electronics component may specifically comprise at least one circuit board having disposed thereon elements of the electronics component. Beyond, the evaluation device may be designed to electrically contact the near-infrared spectrometer device.

Specifically, the system may be configured for performing the method for classifying a sample into one of at least two types of polyamide as described above or as will further be described below in more detail.

In a further aspect of the present invention, a use of a near-infrared spectrometer device for classifying a sample into one of at least two types of polyamide is disclosed.

In a further aspect, a computer program including computer-executable instructions for performing the method according to any one of the embodiments as described herein is disclosed, specifically method steps b) to d), when the program is executed on a computer or computer network, specifically a processor of the device for multiple transition monitoring.

Thus, generally speaking, disclosed and proposed herein is a computer program including computer-executable instructions for performing the method according to the present invention in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, preferably by using a computer program. The computer specifically may be fully or partially integrated into the device for multiple transition monitoring, and the computer programs specifically may be embodied as a software. Alternatively, however, at least part of the computer may also be located outside the device for multiple transition monitoring.

Further disclosed and proposed herein is a computer program product having program code means, in order to perform the method according to the present invention in one or more of the embodiments enclosed herein when the program is executed on a computer or computer network, e.g. one or more of the method steps mentioned above. Specifically, the program code means may be stored on a storage medium such as a computer-readable data carrier.

Further disclosed and proposed herein is a data carrier having a data structure stored thereon, which, after loading into a computer or computer network, such as into a working memory or main memory of the computer or computer network, may execute the method according to one or more of the embodiments disclosed herein, specifically one or more of the method steps mentioned above.

Further disclosed and proposed herein is a computer program product with program code means stored on a machine-readable carrier, in order to perform the method according to one or more of the embodiments disclosed herein, when the program is executed on a computer or computer network, specifically one or more of the method steps mentioned above. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed herein is a modulated data signal which contains instructions readable by a computer system or computer network, for performing the method according to one or more of the embodiments disclosed herein, specifically one or more of the method steps mentioned above.

Further disclosed and proposed herein is a storage medium, wherein a data structure is stored on the storage medium and wherein the data structure is adapted to perform at least steps b), c) and d) of the method according to one or more of the embodiments disclosed herein after having been loaded into a main and/or working storage of a computer or of a computer network.

Specifically, further disclosed herein are:

a computer or computer network comprising at least one processor, wherein the processor is adapted to perform at least steps b), c) and d) of the method according to one of the embodiments described in this description, and a computer loadable data structure that is adapted to perform at least steps b), c) and d) of the method according to one of the embodiments described in this description while the data structure is being executed on a computer.

The method and the system for classifying a sample into one of at least two types of polyamide may have considerable advantages over the prior art. Thus, generally, a handheld NIR spectrometer device may be applicable. Costs may be reduced, time may be saved and a flexible on-site testing, specifically as opposed to lab-based MIR spectrometer devices, may be realized. A non-destructive analysis may be provided due to using NIR technology, specifically as opposed to established melting point tests.

Summarizing, in the context of the present invention, the following embodiments are regarded as particularly preferred:

Embodiment 1: A method for classifying a sample into one of at least two types of polyamide, wherein the method comprises the following steps:

a) providing at least one sample, wherein the sample comprises at least one type of polyamide;
b) acquiring at least one spectrum of the sample using at least one near-infrared spectrometer device;
c) determining at least one peak from the at least one spectrum; and
d) classifying the sample depending on the at least one peak determined from the at least one spectrum into one of the at least two types of polyamide.

Embodiment 2: The method according to the preceding embodiment, wherein step b) comprises determining, and optionally storing on a storage medium, data points representing an absorbance signal, specifically over a wavenumber.

Embodiment 3: The method according to any one of the preceding embodiments, wherein step d) comprises classifying the sample into one of at least two types of polyamide.

Embodiment 4: The method according to the preceding embodiment, wherein the type of polyamide is selected from polyamide 6; polyamide 6.6.

Embodiment 5: The method according to any one of the preceding embodiments, wherein step d) comprises classifying the sample depending on a position of the at least one peak determined from the spectrum.

Embodiment 6: The method according to any one of the preceding embodiments, wherein the spectrum is acquired in a region between 6250 $cm^{-1}$ and 6550 $cm^{-1}$.

Embodiment 7: The method according to any one of the preceding embodiments, wherein the spectrum is acquired in a region between 6150 $cm^{-1}$ and 6550 $cm^{-1}$.

Embodiment 8: The method according to any one of the preceding embodiments, wherein the spectrum of the sample is acquired in a reflectance mode.

Embodiment 9: The method according to any one of the preceding embodiments, wherein the method comprises at least one preprocessing step, wherein the preprocessing step comprises preprocessing the spectrum before step c) is conducted.

Embodiment 10: The method according to the preceding embodiment, wherein the preprocessing step comprises at least one technique selected from the group consisting of: a scatter correction technique; a derivative technique.

Embodiment 11: The method according to the preceding embodiment, wherein the scatter correction technique is selected from the group consisting of: a multiplicative scatter correction; a standard normal variate transform; a robust normal variate transform.

Embodiment 12: The method according to any one of the two preceding embodiments, wherein the derivative technique is selected from the group consisting of: a Norris derivative filter.

Embodiment 13: The method according to any one of the preceding embodiments, wherein a baseline correction is performed before step c) is conducted.

Embodiment 14: The method according to any one of the preceding embodiments, wherein in step c) a peak in a region between 6300 $cm^{-1}$ and 6500 $cm^{-1}$, specifically in a region between 6350 $cm^{-1}$ and 6450 $cm^{-1}$, is determined.

Embodiment 15: The method according to any one of the preceding embodiments, wherein in step c) a peak in a region between 6150 $cm^{-1}$ and 6500 $cm^{-1}$ is determined.

Embodiment 16: The method according to any one of the preceding embodiments, wherein in step c) a fitting procedure of at least a part of the spectrum is performed.

Embodiment 17: The method according to any one of the preceding embodiments, wherein classifying the sample comprises an assignment of at least one numerical value of a property of a peak to at least one pre-defined interval.

Embodiment 18: The method according to the preceding embodiment, wherein the numerical value of the property of the peak corresponds to a wavenumber of the peak.

Embodiment 19: The method according to any one of the two preceding embodiments, wherein classifying the sample comprises an assignment of the at least one numerical value of the property of the peak to at least one first pre-defined interval or to at least one second pre-defined interval.

Embodiment 20: The method according to the preceding embodiment, wherein the first pre-defined interval includes wavenumbers between 6385 $cm^{-1}$ and 6395 $cm^{-1}$.

Embodiment 21: The method according to any one of the two preceding embodiments, wherein the second pre-defined interval includes wavenumbers between 6405 $cm^{-1}$ and 6425 $cm^{-1}$.

Embodiment 22: The method according to any one of the three preceding embodiments, wherein classifying the sample comprises an assignment of the at least one numerical value of the property of the peak to at least one third pre-defined interval.

Embodiment 23: The method according to the preceding embodiment, wherein the third pre-defined interval includes wavenumbers between 6397 $cm^{-1}$ and 6400 $cm^{-1}$.

Embodiment 24: The method according to any one of the five preceding embodiments, wherein the assignment of the at least one numerical value of the property of the peak to the first pre-defined interval or to the second pre-defined interval includes classifying the sample into one of at least two types of polyamide.

Embodiment 25: The method according to any one of the preceding embodiments, wherein the method further comprises at least one confirmation step, wherein the confirmation step comprises classifying the sample depending on at least one further property of the spectrum which differs from the peak of the spectrum.

Embodiment 26: The method according to the preceding embodiment, wherein the confirmation step comprises determining at least one first mean absorbance within at least one first pre-defined wavenumber interval.

Embodiment 27: The method according to the preceding embodiment, wherein the first pre-defined wavenumber interval includes wavenumbers between 6294 $cm^{-1}$ and 6366 $cm^{-1}$.

Embodiment 28: The method according to any one of the three preceding embodiments, wherein the confirmation step comprises determining at least one second mean absorbance within at least one second pre-defined wavenumber interval.

Embodiment 29: The method according to the preceding embodiment, wherein the second pre-defined wavenumber interval includes wavenumbers between 6406 $cm^{-1}$ and 6494 $cm^{-1}$.

Embodiment 30: A system for classifying a sample into one of at least two types of polyamide, wherein the system comprises:

- at least one near-infrared spectrometer device, wherein the near-infrared spectrometer device is configured for acquiring at least one spectrum of a sample; and
- at least one evaluation device, wherein the evaluation device is configured for determining at least one peak from the at least one spectrum and for classifying the sample depending on the at least one peak determined from the at least one spectrum into one of the at least two types of polyamide.

Embodiment 31: The system according to the preceding embodiment, wherein the system is configured for performing the method for classifying a sample into one of at least two types of polyamide according to any one of the preceding claims referring to a method for classifying a sample into one of at least two types of polyamide.

Embodiment 32: A use of a near-infrared spectrometer device for classifying a sample into one of at least two types of polyamide.

Embodiment 33: A computer or computer network comprising at least one processor, wherein the processor is adapted to perform at least steps b), c) and d) of the method for classifying a sample into one of at least two types of polyamide according to any one of the preceding embodiments referring to a method for classifying a sample into one of at least two types of polyamide.

Embodiment 34: A computer loadable data structure that is adapted to perform at least steps b), c) and d) of the method for classifying a sample into one of at least two types of polyamide according to any one of the preceding embodiments referring to a method for classifying a sample into one of at least two types of polyamide while the data structure is being executed on a computer.

Embodiment 35: A computer program, wherein the computer program is adapted to perform at least steps b), c) and d) of the method for classifying a sample into one of at least two types of polyamide according to any one of the preceding embodiments referring to a method for classifying a sample into one of at least two types of polyamide while the program is being executed on a computer.

Embodiment 36: A computer program comprising program means for performing at least steps b), c) and d) of the method for classifying a sample into one of at least two types of polyamide according to any one of the preceding embodiments referring to a method for classifying a sample into one of at least two types of polyamide while the computer program is being executed on a computer or on a computer network.

Embodiment 37: A computer program comprising program means according to the preceding embodiment, wherein the program means are stored on a storage medium readable to a computer.

Embodiment 38: A storage medium, wherein a data structure is stored on the storage medium and wherein the data structure is adapted to perform at least steps b), c) and d) of the method for classifying a sample into one of at least two types of polyamide according to any one of the preceding embodiments referring to a method for classifying a sample into one of at least two types of polyamide after having been loaded into a main and/or working storage of a computer or of a computer network.

Embodiment 39: A computer program product having program code means, wherein the program code means can be stored or are stored on a storage medium, for performing at least steps b), c) and d) of the method for classifying a sample into one of at least two types of polyamide according to any one of the preceding embodiments referring to a method for classifying a sample into one of at least two types of polyamide when the program code means are executed on a computer or on a computer network.

BRIEF DESCRIPTION OF THE FIGURES

Further optional details and features of the invention are evident from the description of preferred exemplary embodiments which follows in conjunction with the dependent claims. In this context, the particular features may be implemented alone or with features in combination.

The invention is not restricted to the exemplary embodiments. The exemplary embodiments are shown schematically in the figures. Identical reference numerals in the individual figures refer to identical elements or elements with identical function, or elements which correspond to one another with regard to their functions.

Specifically, in the figures:

Figure 1:
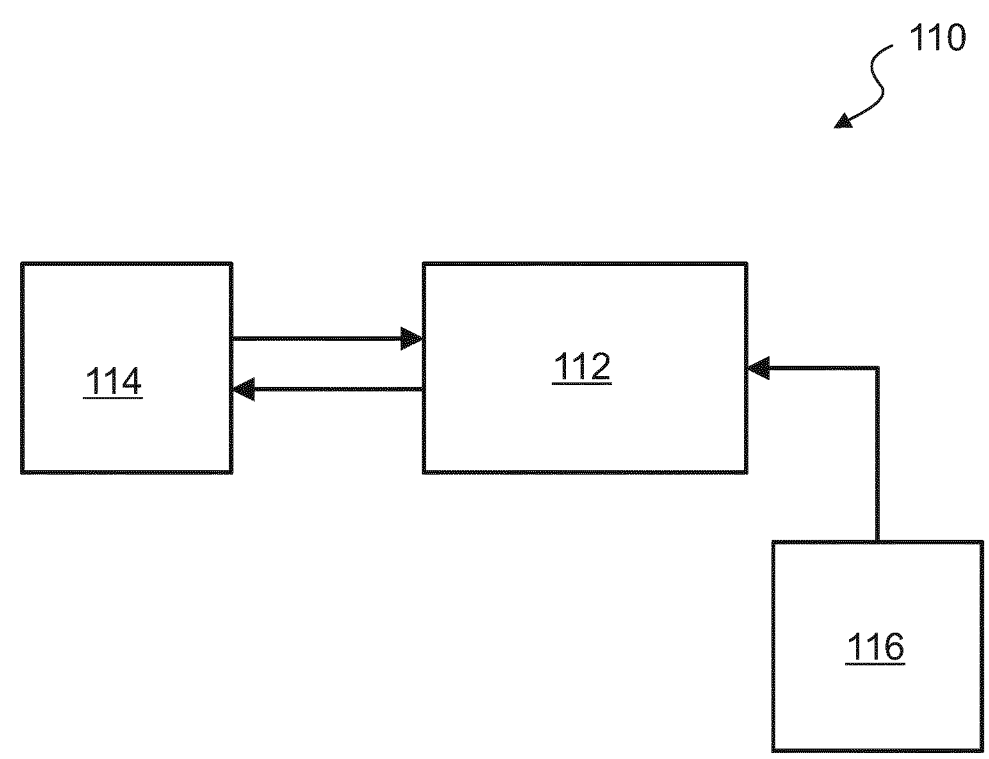
Figure 2A:
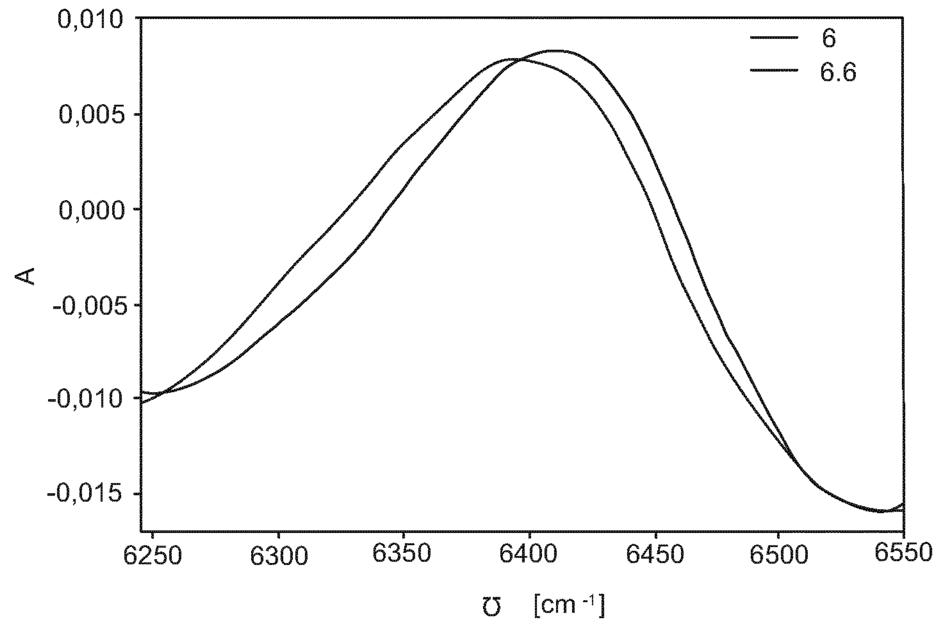
Figure 2B:
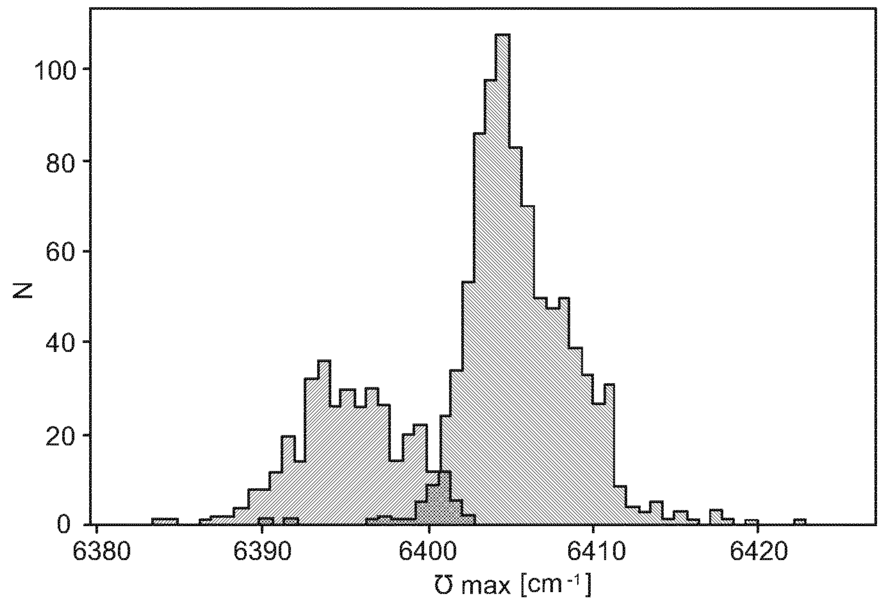
Figure 2C:
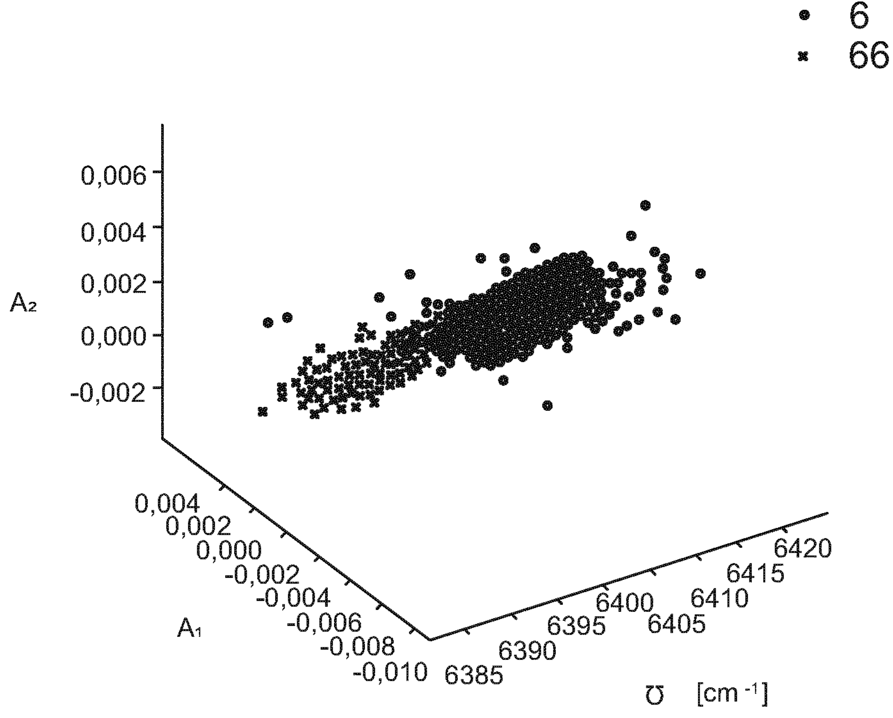

FIG. 1 shows an exemplary embodiment of a system for classifying a sample into one of at least two types of polyamide according to the present invention in a schematic view; and FIGS. 2A to 2C show a comparison of exemplary preprocessed PA 6 and PA 6.6 spectra obtained with a system (FIG. 2A), a histogram plot of estimated peak positions in 1253 spectra of 87 PA 6/6.6 samples that were measured with four different systems (FIG. 2B) and a distribution plot showing peak positions as well as mean absorbances in the intervals [6294,6366] $cm^{-1}$ and [6406,6494] $cm^{-1}$ (FIG. 2C).

EXEMPLARY EMBODIMENTS

FIG. 1 shows an exemplary embodiment of a system 110 for classifying a sample 114 into one of at least two types of polyamide according to the present invention in a schematic view.

The system 110 comprises at least one near-infrared spectrometer device 112. The near-infrared spectrometer device 112 is configured for acquiring at least one spectrum of a sample 114. Further, the system 110 comprises at least one evaluation device 116. The evaluation device 116 is configured for determining at least one peak from the spectrum and for classifying the sample 114 depending on the at least one peak determined from the spectrum. For further details on the near-infrared spectrometer device 112, the evaluation device 116 and the sample 114 reference is made to the description above.

FIG. 2A shows a comparison of exemplary preprocessed PA 6 and PA 6.6 spectra obtained with a system 110 as schematically illustrated in FIG. 1. In FIG. 2A the preprocessed absorbance A is illustrated in dependence on the wavenumber v. Further, FIG. 2B shows a histogram plot of estimated peak positions in 1253 spectra of 87 PA 6/6.6 samples that were measured with four different systems 110. Specifically, in FIG. 2B, the number of spectra N is shown in dependence on the peak position $v_{max}$. Further, FIG. 2C shows a distribution plot showing peak positions $v_{max}$ as well as mean absorbances $A_1$ and $A_2$ in the intervals [6294, 6366] $cm^{-1}$ and [6406,6494] $cm^{-1}$.

The spectra as illustrated in FIG. 2A were preprocessed. Specifically, a baseline correction was conducted. Further, a scatter correction by using a robust normal variate transform (percentile=25%) was performed and a Norris derivative filter (second derivative, window size of 15 pixels) was applied. As illustrated in FIG. 2A, in a spectrum that is preprocessed in this manner, a peak emerges in the region between 6300 $cm^{-1}$ and 6500 $cm^{-1}$, specifically close to 6400 $cm^{-1}$. The peak can was fitted using an analytical description (e.g., a second-order polynomial) and by employing the zero-crossing point of its first derivative. The position of the peak in the preprocessed spectrum was used to distinguish between PA 6 and PA 6.6. The latter peak is generally shifted towards lower wavenumbers (higher wavelengths) for PA 6.6 as compared to PA 6, as illustrated in FIGS. 2A and 2B. In FIG. 2A, the thick line represents a spectrum obtained from a polyamide 6 sample and the thin line represents a spectrum obtained from a polyamide 6.6 sample.

More stable classifications were achieved by adding additional features in the wings of the peak profile, i.e., by determining the mean value of the preprocessed absorbances in the regions from 6294 $cm^{-1}$ to 6366 $cm^{-1}$ and from 6406 $cm^{-1}$ to 6494 $cm^{-1}$. The feature distribution can then be fitted by means of, e.g., a support vector classifier, or other supervised learning classifiers. In FIG. 2C, the separation between spectra attributable to PA 6 and PA 6.6, respectively, is again clearly identifiable.

LIST OF REFERENCE NUMBERS

110 system
112 near-infrared spectrometer device
114 sample
116 evaluation device

The invention claimed is:

1. A method for classifying a sample into one of at least two types of polyamide, wherein the method comprises the following steps:

a) providing at least one sample, wherein the sample comprises at least one type of polyamide;
b) acquiring at least one spectrum of the sample using at least one near-infrared spectrometer device;
c) determining at least one peak from the at least one spectrum, wherein a peak in a region between 6300 $cm^{-1}$ and 6500 $cm^{-1}$ is determined; and
d) classifying the sample depending on the at least one peak determined from the at least one spectrum into one of the at least two types of polyamide.

2. The method according to the claim 1, wherein the type of polyamide is polyamide 6 or polyamide 6.6.

3. The method according to claim 1, wherein step d) comprises classifying the sample depending on a position of the at least one peak determined from the at least one spectrum.

4. The method according to claim 1, wherein the at least one spectrum is acquired in a region of from 6250 $cm^{-1}$ to 6550 $cm^{-1}$.

5. The method according to claim 1, wherein the method comprises at least one preprocessing step, wherein the preprocessing step comprises preprocessing the at least one spectrum before step c) is conducted, wherein the preprocessing step comprises at least one technique selected from the group consisting of a scatter correction technique and a derivative technique.

6. The method according to claim 1, wherein a baseline correction is performed before step c) is conducted.

7. The method according to claim 1, wherein classifying the sample comprises an assignment of at least one numerical value of a property of a peak to at least one pre-defined interval.

8. The method according to claim 7, wherein the property of the peak corresponds to a wavenumber of the peak.

9. The method according to claim 7, wherein classifying the sample comprises an assignment of the at least one numerical value of the property of the peak to at least one first pre-defined interval or to at least one second pre-defined interval.

10. The method according to claim 9, wherein the assignment of the at least one numerical value of the property of the peak to the first pre-defined interval or to the second pre-defined interval comprises classifying the sample into one of at least two types of polyamide.

11. The method according to claim 1, wherein the method further comprises at least one confirmation step, wherein the confirmation step comprises classifying the sample depending on at least one further property of the at least one spectrum which differs from the peak of the at least one spectrum.

12. The method according to claim 11, wherein the confirmation step comprises determining at least one first mean absorbance within at least one first pre-defined wavenumber interval, wherein the confirmation step comprises determining at least one second mean absorbance within at least one second pre-defined wavenumber interval.

13. A system for classifying a sample into one of at least two types of polyamide, wherein the system comprises:

at least one near-infrared spectrometer device, wherein the near-infrared spectrometer device is configured for acquiring at least one spectrum of a sample; and at least one evaluation device, wherein the evaluation device is configured for determining at least one peak from the at least one spectrum in a region between 6300 $cm^{-1}$ and 6500 $cm^{-1}$and for classifying the sample depending on the at least one peak determined from the at least one spectrum into one of the at least two types of polyamide.

14. A method of using the system according to claim 13, the method comprising using the system for classifying a sample into one of at least two types of polyamide, wherein the method comprises the following steps:

a) providing at least one sample, wherein the sample comprises at least one type of polyamide;

b) acquiring at least one spectrum of the sample using the at least one near-infrared spectrometer device;

c) determining at least one peak from the at least one spectrum, wherein a peak in a region between 6300 cm-1 and 6500 cm-1 is determined; and d) classifying the sample depending on the at least one peak determined from the at least one spectrum into one of the at least two types of polyamide.

* * * * *